US012721998B2

(12) United States Patent
Masko et al.

(10) Patent No.: US 12,721,998 B2
(45) Date of Patent: Sep. 1, 2026

(54) MEDICAL ELECTRODE

(71) Applicant: i-Lumen Scientific, Inc., Bloomington, MN (US)

(72) Inventors: Marshall T. Masko, Minnetonka, MN (US); John C. VeLure, Minnetonka, MN (US); Thu-Ha Duncan, Cleveland, TN (US)

(73) Assignee: i-Lumen Scientific, Inc., Bloomington, MN (US)

( * ) Notice: Subject to any disclaimer, the term of this patent is extended or adjusted under 35 U.S.C. 154(b) by 0 days.

(21) Appl. No.: 18/715,075

(22) PCT Filed: Nov. 28, 2022

(86) PCT No.: PCT/US2022/051076
§ 371 (c)(1),
(2) Date: May 30, 2024

(87) PCT Pub. No.: WO2023/101910
PCT Pub. Date: Jun. 8, 2023

(65) Prior Publication Data
US 2025/0177730 A1 Jun. 5, 2025

(51) Int. Cl.
*A61N 1/04* (2006.01)
*A61N 1/36* (2006.01)

(52) U.S. Cl.
CPC ......... *A61N 1/0492* (2013.01); *A61N 1/3603* (2017.08); *A61N 1/36046* (2013.01)

(58) Field of Classification Search
CPC ............................ A61N 1/0492; A61N 1/0456
See application file for complete search history.

(56) References Cited

U.S. PATENT DOCUMENTS 3,669,119 A 6/1972 Symmes
6,298,255 B1 10/2001 Cordero et al.
(Continued)

FOREIGN PATENT DOCUMENTS

JP D2019-5831 7/2019
WO 2020210471 A1 10/2020
(Continued)

OTHER PUBLICATIONS

I-Lumen Scientific, Inc.—Virtual Rocket Pitch presentation at CONNECTpreneur. Online, published date Oct. 14, 2021. Retrieved on Jul. 21, 2023 from URL: https://www.youtube.com/watch?v=iv6vA7D _ngo.
(Continued)

*Primary Examiner* — Rochelle D Turchen
(74) *Attorney, Agent, or Firm* — Fox Rothschild LLP

(57) ABSTRACT

A system that includes a first electrode substrate having a first end and a second end, wherein the first electrode substrate includes one or more electrodes on the first electrode substrate configured to apply electrical-stimulation therapy to a first eye of a patient, wherein the first electrode substrate is configured to locate the one or more electrodes on an outer surface of at least one of the upper eyelid and the lower eyelid of the patient's first eye, a first plurality of adhesive patches coupled to the first electrode substrate and configured to secure the first electrode substrate to the patient, wherein the first plurality of adhesive patches includes a first adhesive patch and a second adhesive patch; and a stimulation controller configured to control the electrical-stimulation therapy, wherein each of the one or more electrodes of the first electrode substrate is operatively coupled to the stimulation controller.

22 Claims, 5 Drawing Sheets

(56) References Cited

U.S. PATENT DOCUMENTS

| | | | |
|---|---|---|---|
| 6,792,314 B2 | 9/2004 | Byers et al. | |
| D633,621 S | 3/2011 | Yuen et al. | |
| 8,188,433 B2 | 5/2012 | Gonopolskiy et al. | |
| D779,432 S | 2/2017 | Wong et al. | |
| D790,069 S | 6/2017 | Wong et al. | |
| D854,697 S | 7/2019 | Yang | |
| D860,465 S | 9/2019 | Lovell et al. | |
| D880,701 S | 4/2020 | Oz et al. | |
| D905,858 S | 12/2020 | Lovell et al. | |
| D927,005 S | 8/2021 | Hauser-Raspe et al. | |
| 11,116,973 B1 | 9/2021 | Masko et al. | |
| D936,843 S | 11/2021 | Besko et al. | |
| D970,018 S | 11/2022 | Soosalu et al. | |
| D971,415 S | 11/2022 | Treen et al. | |
| D1,010,832 S | 1/2024 | Masko et al. | |
| D1,029,275 S | 5/2024 | Huang et al. | |
| D1,030,071 S | 6/2024 | Huang et al. | |
| 2005/0085741 A1* | 4/2005 | Hoskonen | A61B 5/388 600/300 |
| 2011/0160639 A1 | 6/2011 | Yanaki | |
| 2014/0073895 A1 | 3/2014 | Freeman et al. | |
| 2015/0190629 A1 | 7/2015 | Mohn et al. | |
| 2016/0089534 A1 | 3/2016 | Mohammadi et al. | |
| 2017/0246446 A1 | 8/2017 | Lee et al. | |
| 2017/0290525 A1 | 10/2017 | Waites et al. | |
| 2019/0143116 A1 | 5/2019 | Mowery et al. | |
| 2020/0324114 A1 | 10/2020 | Chiapetta et al. | |
| 2020/0391029 A1 | 12/2020 | Mullins et al. | |
| 2022/0296899 A1* | 9/2022 | Rockley | A61N 1/0492 |

FOREIGN PATENT DOCUMENTS

| | | |
|---|---|---|
| WO | 2021011255 A1 | 1/2021 |
| WO | 2021/185423 A1 | 9/2021 |

OTHER PUBLICATIONS

Extended European Search Report for European Application No. 22902051.6, filed Jun. 5, 2024 mailed Dec. 12, 2025.

* cited by examiner

MEDICAL ELECTRODE

CROSS-REFERENCE TO RELATED APPLICATIONS

This application is a National Phase under 35 U.S.C. § 371 of International Application No. PCT/US22/51076, filed Nov. 28, 2022, which is incorporated herein by reference in its entirety.

This application is related to:

U.S. Pat. No. 10,391,312, issued on Aug. 27, 2019 by Mowery et al., titled "APPARATUS AND METHOD FOR OCULAR MICROCURRENT STIMULATION THERAPY," PCT Patent Application PCT/US2016/051550 (published as WO 2017/048731), filed Sep. 13, 2016 by Mowery et al., titled "APPARATUS AND METHOD FOR OCULAR MICROCURRENT STIMULATION THERAPY,"

U.S. Provisional Patent Application 62/283,870, filed Sep. 15, 2015 by Mowery et al., titled "APPLIANCE FOR MICROCURRENT STIMULATION THERAPY USING A DISPOSABLE MATERIAL AFIXED TO THE UPPER AND LOWER EYE LID & OTHER BODY PARTS,"

U.S. Provisional Patent Application 62/283,871, filed Sep. 15, 2015 by Masko et al., titled "APPARATUS FOR A METHOD OF APPLICATION OF MICROCURRENT STIMULATION THERAPY, CONSISTING OF A GOGGLE DEVICE AFFIXED TO & ENCIRCLING THE UPPER AND/OR LOWER EYELIDS, AS WELL AS OTHER BODY PARTS,"

U.S. Provisional Patent Application 62/365,838, filed Jul. 22, 2016 by Tapp et al., titled "APPLIANCE FOR MICRO-CURRENT STIMULATION,"

U.S. patent application Ser. No. 17/415,508 (published as US 2022/0047866), filed Jun. 17, 2021 by Masko et al., titled "APPARATUS AND METHOD FOR MICRO-CURRENT STIMULATION THERAPY,"

U.S. patent application Ser. No. 17/416,024, filed Jun. 18, 2021 by Masko et al., titled "MICROCURRENT-STIMULATION-THERAPY APPARATUS AND METHOD" (issued Sep. 13, 2022 as U.S. Pat. No. 11,439,823), PCT Patent Application PCT/US2019/063404 (published as WO 2020/131329), filed on Nov. 26, 2019, by Masko et al., titled "APPARATUS AND METHOD FOR MICROCURRENT STIMULATION THERAPY,"

PCT Application PCT/US2019/067627 (published as WO 2020/132337), filed on Dec. 19, 2019 by Masko et al., titled "MICROCURRENT-STIMULATION-THERAPY APPARATUS AND METHOD,"

U.S. Provisional Patent Application 62/783,116 filed on Dec. 20, 2018 by Masko et al., titled "APPARATUS AND METHOD FOR MICROCURRENT STIMULATION THERAPY,"

PCT Patent Application PCT/US2020/021267 (published as WO 2021/177968), filed Mar. 5, 2020 by Mowery et al. titled "VISION TESTING AND TREATMENT SYSTEM AND METHOD,"

PCT Patent Application PCT/US2021/031869 (published as WO 2021/231496), filed May 11, 2021 by Duncan et al. titled "ELECTRODE SYSTEM FOR VISION TREATMENT AND METHOD,"

U.S. Provisional Patent Application 63/025,987 filed on May 15, 2020 by Duncan et al., titled "ELECTRODE SYSTEM FOR VISION TREATMENT AND METHOD,"

U.S. Pat. No. 11,116,973, issued Sep. 14, 2021 to Masko et al., titled "SYSTEM AND METHOD FOR A MEDICAL DEVICE," and U.S. Provisional Patent Application 63/281,558 filed on Nov. 19, 2021 by Masko et al., titled "METHOD AND SYSTEM FOR EYE TREATMENT," each of which is incorporated herein by reference in its entirety.

FIELD OF THE INVENTION

The present invention relates to medical electrode systems and more particularly to an electrode system configured for placement on a patient's upper and/or lower eyelid, such as for application of microcurrent stimulation and/or sensing.

BACKGROUND

U.S. Pat. No. 5,522,864 by Larry B. Wallace et al., issued on Jun. 4, 1996 with the title "Apparatus and method for ocular treatment," and is incorporated herein by reference. U.S. Pat. No. 5,522,864 describes that macular degeneration and other ocular pathology in a subject are treated by the steps of: placing a positive electrode of a direct current source in electrical contact with a closed eyelid of a subject; placing a negative electrode of the source in electrical contact with the posterior neck of the subject; and causing a constant direct current of 200 μA to flow between the electrodes through the subject for about 10 minutes. The source can be a portable, battery powered constant direct current generator which is affixed to the subject. The subject can ambulate during treatment.

U.S. Pat. No. 6,035,236 by John B. Jarding, et al., issued on Mar. 7, 2000 with the title "Methods and apparatus for electrical microcurrent stimulation therapy" and is incorporated herein by reference in its entirety. U.S. Pat. No. 6,035,236 describes an apparatus for supplying an electrical signal to a body part in order to provide microcurrent stimulation therapy to the body part. The apparatus preferably includes a first sweep wave or sweep frequency signal generator configured to generate a first sweep wave signal, a buffer amplifier circuit configured to receive the first sweep wave signal from the first sweep signal generator and amplify and buffer the sweep wave signal creating a buffered sweep wave signal. In addition, the apparatus preferably includes a current limiting circuit configured to receive the buffered sweep wave signal from the buffer amplifier circuit and limit the amount of current supplied to the body part. Finally, the apparatus preferably comprises a probe for applying the sweep wave signal to the body part. The apparatus may further comprise a second signal generator for generating a second signal which may comprise either a sweep wave signal or a non-sweep wave signal. The apparatus also will include a signal combining circuit configured to receive the first and second signals from the first and second signal generators and combine the first and second signals into a composite sweep wave signal.

U.S. Pat. No. 6,275,735 by John B. Jarding et al., issued on Aug. 14, 2001 with the title "Methods and apparatus for electrical microcurrent stimulation therapy" and is incorporated herein by reference in its entirety. U.S. Pat. No. 6,275,735 describes a method and apparatus for providing microcurrent stimulation therapy to a body part. In one embodiment, a method allows digital control of the modulation frequency of the microcurrent signal. The method includes receiving a first digital data word which is used to produce a first frequency related to the first digital data word, whereupon, a first microcurrent signal at the first frequency is applied to the body part. A second digital data word is received and used to produce a second frequency related to the second digital data word. A second microcurrent signal at the second frequency is applied to the body part. In another embodiment, a method allows direct digital synthesis of the microcurrent stimulation signal. A first digital data word is used to produce a first analog voltage which is applied to the body part. A second digital data word is used to produce a second analog voltage which is also applied to the body part, where the first analog voltage is different from the second analog voltage. In yet another embodiment, an apparatus for providing microcurrent stimulation therapy includes a digital-to-analog converter, a controller and a plurality of data words. The controller is coupled to the digital-to-analog converter and supplies the digital-to-analog converter with digital data words in order to generate an electrical signal for the microcurrent stimulation therapy.

U.S. Pat. No. 7,062,319 by Jouni Ihme, et al., issued on Jun. 13, 2006 with the title "Method and arrangement for determining suitable treatment frequency and/or intensity," and is incorporated herein by reference. U.S. Pat. No. 7,062,319 describes a method and arrangement for determining a suitable treatment frequency and/or intensity of a treatment signal used in electrical treatment. In the method, a stimulating electrical signal is directed to an object to produce different reaction types in the object at different intensities of the stimulating electrical signal. For at least three different reaction types, the intensity of the stimulating electrical signal at which a reaction type occurred is stored. The electrical signal intensities stored for the different reaction types at least at three different frequencies are compared with reference values and the frequency and/or signal intensity at which the signal intensity deviates sufficiently from one or more reference values is determined. The method utilizes the frequency and/or signal intensity found in the process in determining the suitable treatment frequency and/or signal intensity.

U.S. Pat. No. 7,158,834 by Edward L. Paul, Jr., issued on Jan. 2, 2007 with the title "Method and apparatus for performing microcurrent stimulation (MSC) therapy," and is incorporated herein by reference. U.S. Pat. No. 7,158,834 describes a method and apparatus for providing microcurrent stimulation (MSC) therapy. U.S. Pat. No. 7,158,834 states: it has been determined that the application of microcurrent signals at particular frequencies to the eye for particular periods of time stabilizes and even improves conditions of macular degeneration and other ocular diseases.

U.S. Pat. No. 7,326,181 by Jefferson J. Katims, issued on Feb. 5, 2008 with the title "Nervous tissue stimulation device and method," and is incorporated herein by reference. U.S. Pat. No. 7,326,181 describes a method using a precisely controlled, computer programmable stimulus for neuroselective tissue stimulation that does not leave a sufficient voltage or electrical artifact on the tissue being stimulated that would interfere or prevent a monitoring system from recording the physiological response is utilized to evaluate the physiological conduction of the tissue being studied. A computer controls both the waveform, duration and intensity of the stimulus. An output trigger to the nerve response recording component controls the timing of its operation. A neuroselective nervous tissue response latency and amplitude may be determined. The computer controlled stimulus may also be administered for therapeutic purposes.

U.S. Pat. No. 8,843,209 by Paul W. Wacnik et al., issued on Sep. 23, 2014 with the title "Ramping parameter values for electrical stimulation therapy," and is incorporated herein by reference. U.S. Pat. No. 8,843,209 describes devices, systems, and techniques for ramping one or more parameter values of electrical stimulation. An implantable medical device may increase or decrease a parameter value, e.g., amplitude or pulse width, over time to reach a target value of the parameter. In one example, a memory may be configured to store a plurality of amplitude ramp schedules. At least one processor may be configured to obtain a stimulation parameter set that at least partially defines an electrical stimulation therapy, select one of the plurality of amplitude ramp schedules based on a signal frequency of the stimulation parameter set, and increase an amplitude of the electrical stimulation therapy during a ramp period defined by the selected amplitude ramp schedule.

U.S. Pat. No. 9,724,230 by Paul Badawi, issued on Aug. 8, 2017 with the title "Dry eye treatment apparatus and methods," and is incorporated herein by reference. U.S. Pat. No. 9,724,230 describes dry eye treatment apparatus and methods which generally include a patch or strip affixed to the skin of the upper and/or lower eyelids to deliver heat or other forms of energy, pressure, drugs, moisture, etc. (alone or in combination) to the one or more meibomian glands contained within the underlying skin. The treatment strip or strips include one or more strips configured to adhere to an underlying region of skin in proximity to one or both eyes of a subject such that the one or more strips allow for the subject to blink naturally without restriction from the one or more strips. Moreover, the one or more strips may be configured to emit energy to the underlying region of skin and where the one or more strips are shaped to follow a location of one or more meibomian glands contained within the underlying region of skin.

SUMMARY OF THE INVENTION

In some embodiments, the present invention provides a system that includes a first electrode substrate having a first end and a second end, wherein the first electrode substrate includes one or more electrodes on the first electrode substrate, wherein the one or more electrodes are configured to apply electrical-stimulation therapy to a first eye of a patient, the first eye having an upper eyelid and a lower eyelid, wherein the first electrode substrate is configured to locate the one or more electrodes on an outer surface of at least one of the upper eyelid and the lower eyelid of the patient's first eye; a first plurality of adhesive patches coupled to the first electrode substrate and configured to secure the first electrode substrate to the patient, wherein the first plurality of adhesive patches includes a first adhesive patch and a second adhesive patch; and a stimulation controller configured to control the electrical-stimulation therapy, wherein each of the one or more electrodes of the first electrode substrate is operatively coupled to the stimulation controller.

In some embodiments, the present invention provides a method that includes providing a first electrode substrate having a first end, a second end, and a middle portion located between the first end and the second end, wherein the first electrode substrate includes one or more electrodes on the first electrode substrate, wherein the one or more electrodes are configured to apply electrical-stimulation therapy to a first eye of a patient, the first eye having an upper eyelid and a lower eyelid; placing the first electrode substrate on the patient such that the one or more electrodes are located on an outer surface of at least one of the upper eyelid and the lower eyelid of the patient's first eye; securing the first electrode substrate to the patient; providing a stimulation controller configured to control the electrical-stimulation therapy; and operatively coupling each of the one or more electrodes of the first electrode substrate to the stimulation controller.

In some embodiments, the present invention provides a system that includes a first electrode substrate having a first end, a second end, and a middle portion located between the first end and the second end, wherein the first electrode substrate includes one or more electrodes on the first electrode substrate, wherein the one or more electrodes are configured to apply electrical-stimulation therapy to a first eye of a patient, the first eye having an upper eyelid and a lower eyelid; means for securing the first electrode substrate to the patient such that the one or more electrodes are located on an outer surface of at least one of the upper eyelid and the lower eyelid of the patient's first eye; means for controlling the electrical-stimulation therapy; and means for operatively coupling each of the one or more electrodes of the first electrode substrate to the means for controlling.

DETAILED DESCRIPTION

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The embodiments shown in the Figures and described here may include features that are not included in all specific embodiments. A particular embodiment may include only a subset of all of the features described, or a particular embodiment may include all of the features described.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Figure 1:
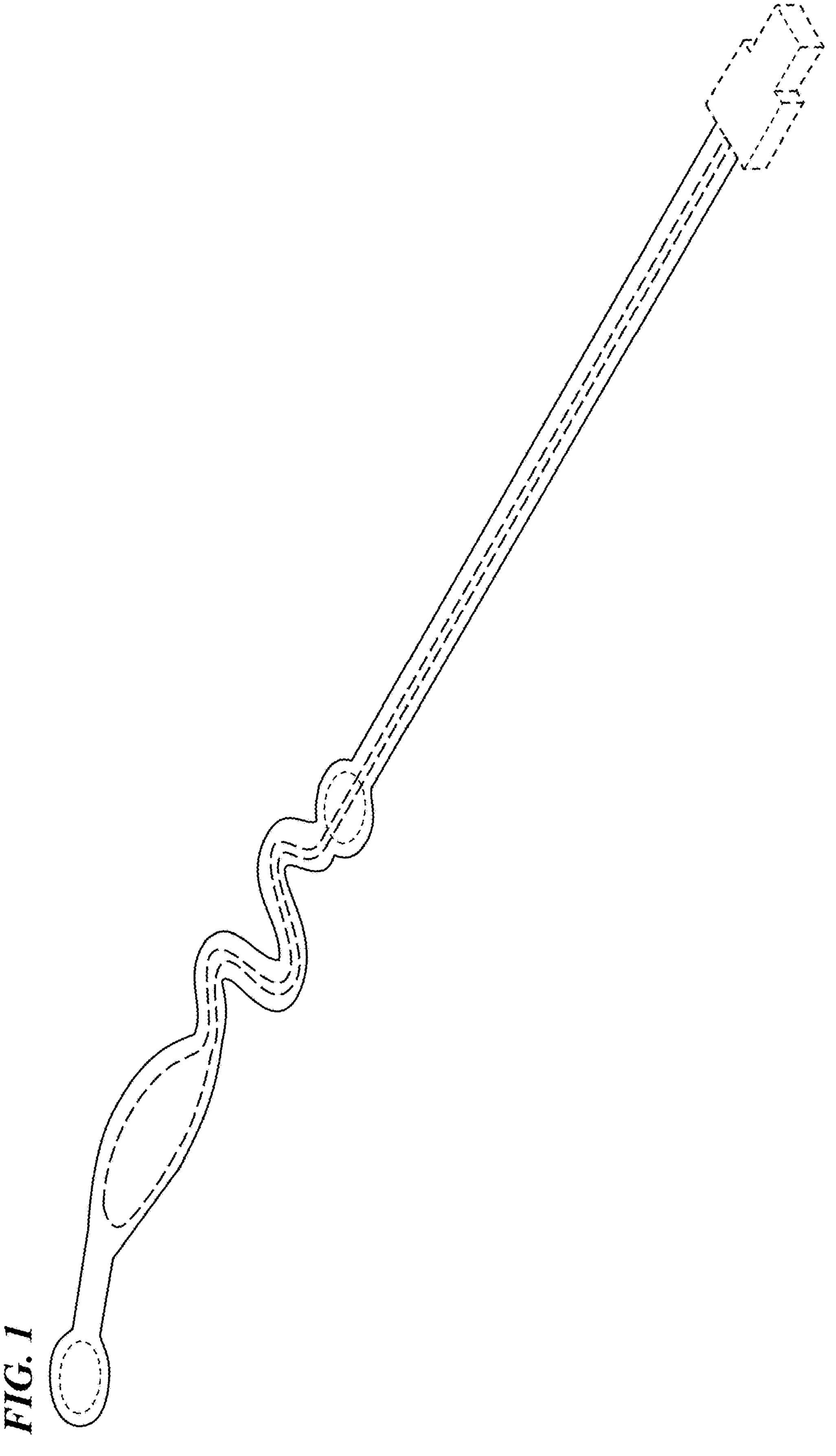
FIG. 1 is perspective view of a medical electrode, according to some embodiments of the present invention.

FIG. 1 is perspective view of a medical electrode, according to some embodiments of the present invention.

Figures 2, 3, 4, 5, 6, 7:
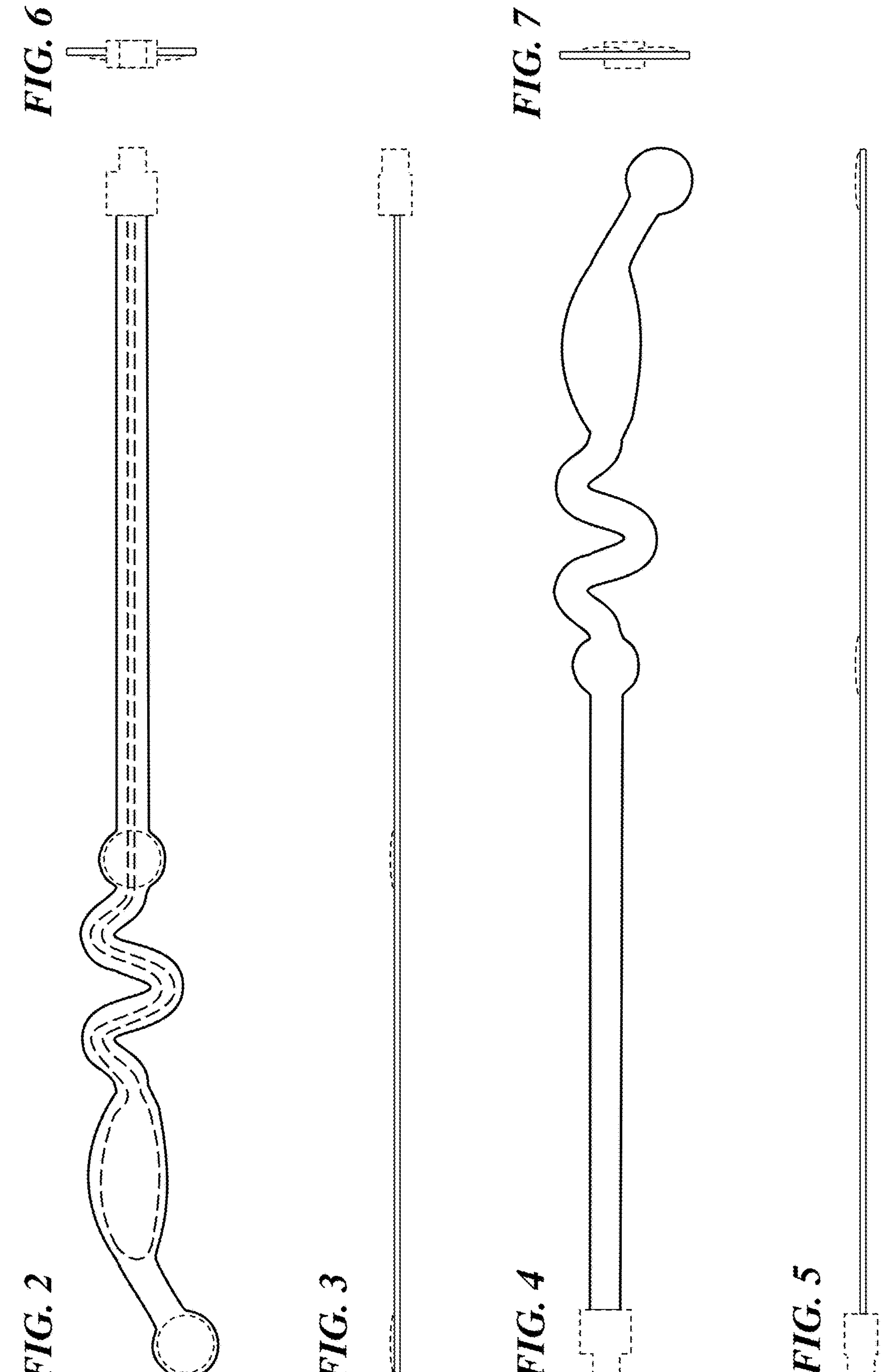
FIG. 2 is a top view of the medical electrode, according to some embodiments of the present invention.
FIG. 3 is a left-side view of the medical electrode, according to some embodiments of the present invention.
FIG. 4 is a bottom view of the medical electrode, according to some embodiments of the present invention.
FIG. 5 is a right-side view of the medical electrode, according to some embodiments of the present invention.
FIG. 6 is a back view of the medical electrode, according to some embodiments of the present invention.
FIG. 7 is a front view of the medical electrode, according to some embodiments of the present invention.

FIG. 2 is a top view of the medical electrode, according to some embodiments of the present invention.

FIG. 3 is a left-side view of the medical electrode, according to some embodiments of the present invention.

FIG. 4 is a bottom view of the medical electrode, according to some embodiments of the present invention.

FIG. 5 is a right-side view of the medical electrode, according to some embodiments of the present invention.

FIG. 6 is a back view of the medical electrode, according to some embodiments of the present invention.

FIG. 7 is a front view of the medical electrode, according to some embodiments of the present invention.

Figure 8:
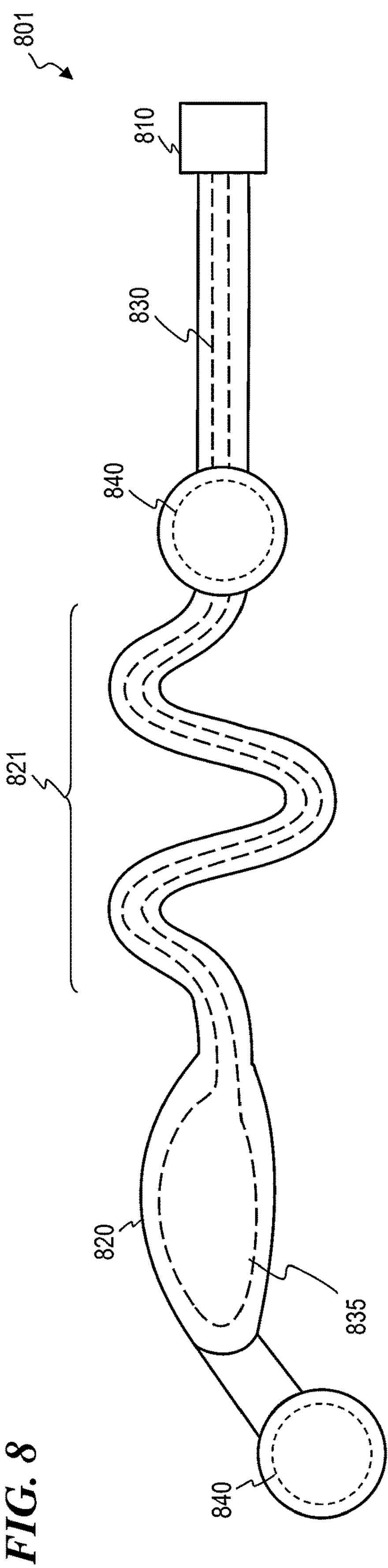
FIG. 8 is a schematic diagram of a medical electrode system 801, according to some embodiments of the present invention.

FIG. 8 is a schematic diagram of a medical electrode system 801, according to some embodiments of the present invention. In some embodiments, medical electrode system 801 is used to provide an electrical stimulation therapy to the eye(s) of the patient such as the stimulation therapies described in U.S. Pat. No. 10,391,312, which is incorporated by reference above. In some embodiments, medical electrode system 801 includes an electrode 835 and an electrical pathway 830 affixed to a substrate 820. In some embodiments, electrode 835 is operatively coupled to an electrical connector 810 by electrical pathway 830. In some embodiments, system 801 includes one or more adhesive pads 840 configured to hold system 801 in place during an electrical stimulation treatment (e.g., in some embodiments, a first adhesive pad 840 (e.g., the adhesive pad 840 closest to electrode 835) is configured to be placed on or near the side of the nose of the patient and a second adhesive pad 840 (e.g., the adhesive pad 840 closest to connector 810) is configured to be placed on the temple of the patient). In some embodiments, substrate 820 includes a flexible section 821 configured to allow size adjustments (e.g., in some embodiments, section 821 is stretchable such that the length of section 821 can be varied) in order to ensure that system 801 can fit varying patient face sizes.

Figure 9A:
FIG. 9A is a schematic side-view of an electrical stimulation system 901 positioned on a patient 99, according to some embodiments of the present invention.
Figure 9A:
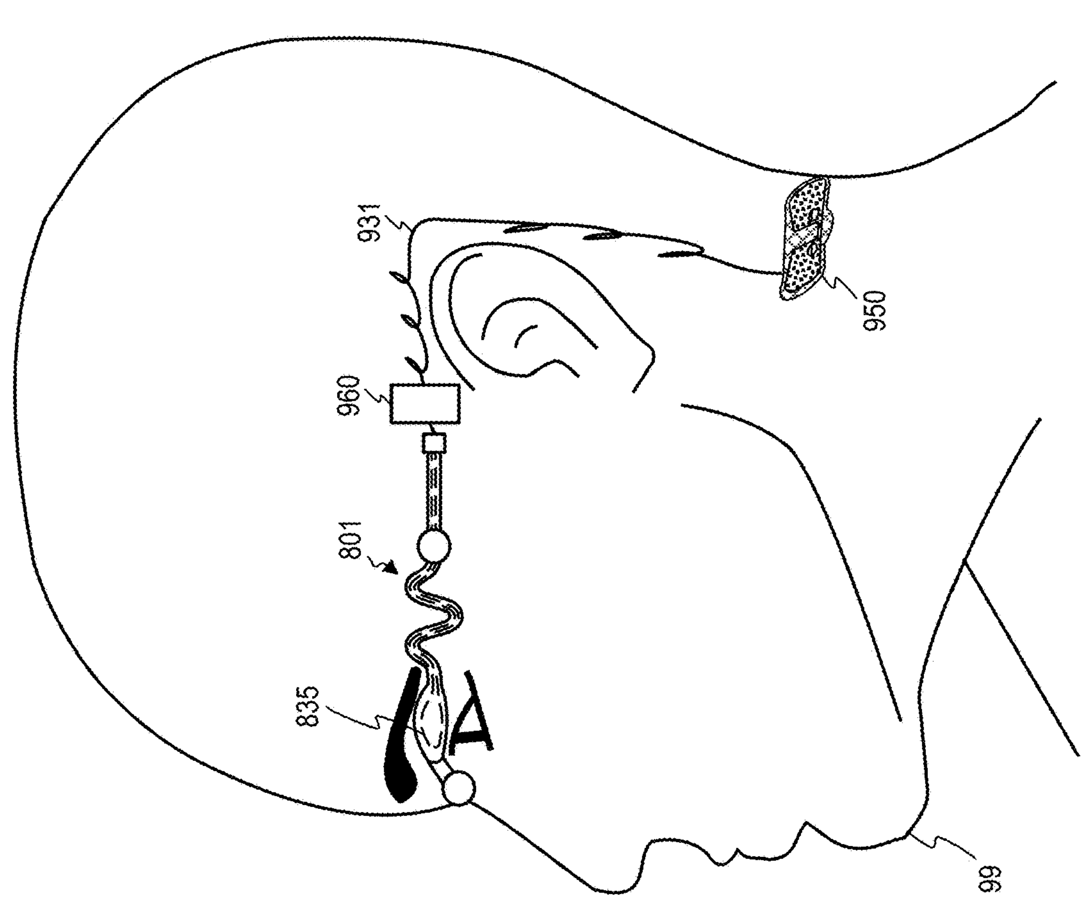

FIG. 9A is a schematic side-view of an electrical stimulation system 901 positioned on a patient 99, according to some embodiments of the present invention. In some embodiments, stimulation system 901 includes medical electrode system 801 placed on patient 99 such that electrode 835 is affixed to the upper eyelid of patient 99, return (ground) electrode 950 placed on the back of the neck of patient 99, and stimulation controller 960 operatively coupled to both return electrode 950 (e.g., in some embodiments, a return-electrode system such as described in PCT/US2021/031869 (published as WO 2021/231496), which is incorporated by reference above) and medical electrode system 801 via an electrical connection 931 (e.g., in some embodiments, a wire). In some embodiments, a duplicate of medical electrode system 801 is located on the other side of patient 99 and is configured to communicate (wirelessly or via a wired connection) with system 801. In some embodiments, system 801 and its duplicate on the other side of patient 99 each include a respective therapy controller 960 coupled to a corresponding ground electrode 950. In other embodiments, system 801 and its duplicate are controlled by a single therapy controller 960 and are coupled to a single ground electrode 950. In some embodiments, controller 960 is operatively coupled to a remote laptop or other remote computer device (e.g., a smartphone) via a wired or wireless connection.

Figures 9B, 9C:
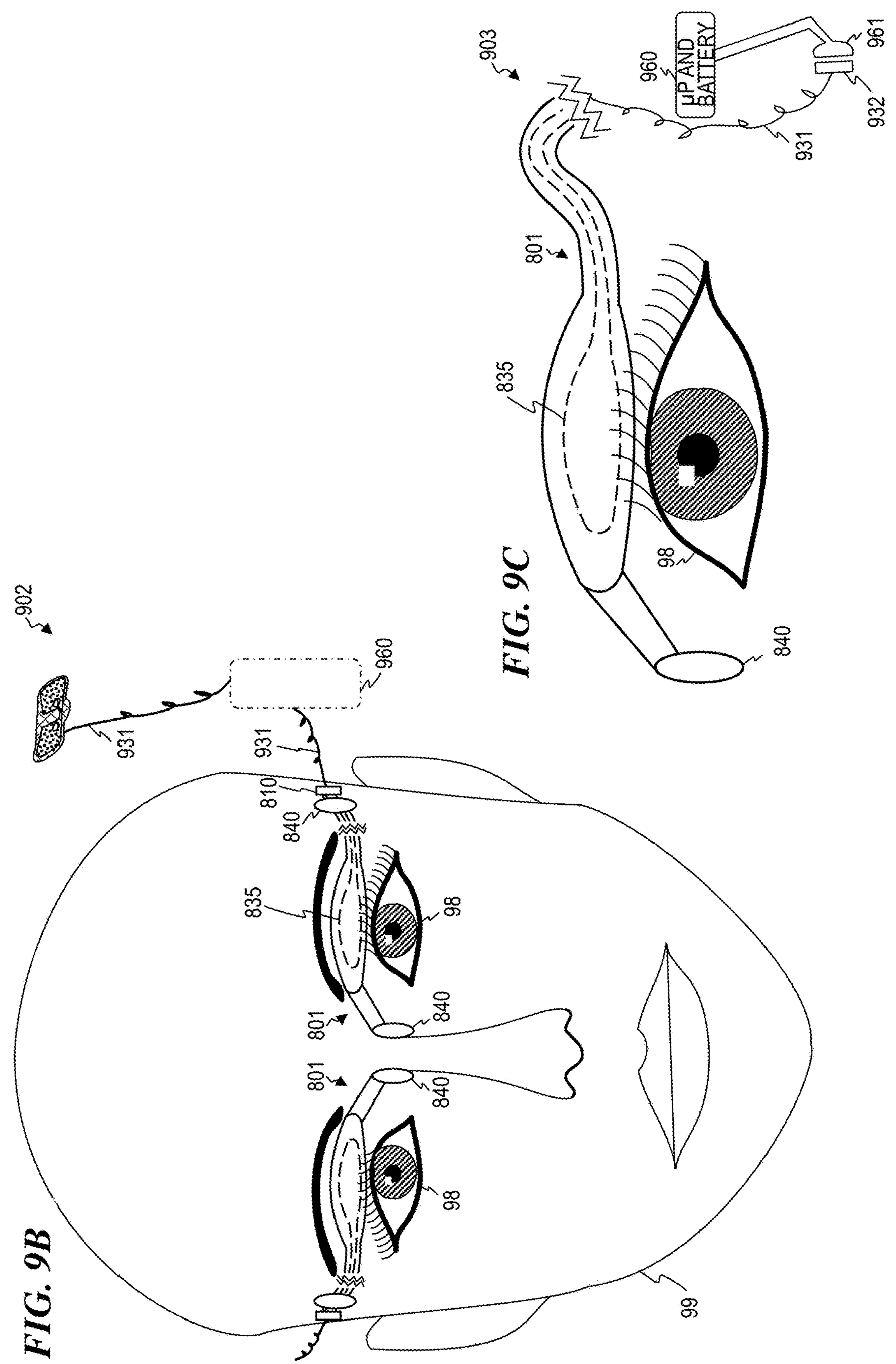
FIG. 9B is a schematic front-view diagram of an electrical stimulation system 902 positioned on patient 99, according to some embodiments of the present invention.
FIG. 9C is a magnified front view of an electrical stimulation system 903 positioned at eye 98, according to some embodiments of the present invention.

FIG. 9B is a schematic front-view diagram of an electrical stimulation system 902 positioned on patient 99, according to some embodiments of the present invention. In some embodiments, system 902 is substantially similar to system 901 except that two duplicate systems 801 are shown in system 902 of FIG. 9B (one for each eye). In some embodiments, controller 960 is located locally (e.g., in a battery operated unit that is carried by patient 99, such as in a shirt pocket or head-mounted elastic band or in/on an cable-holder like, for example, cable-holder system 1501 of FIGS. 15A-15B of U.S. Pat. No. 11,116,973, which is incorporated by reference above), while in other embodiments, controller 960 is attached to or part of a computer-controlled apparatus such as a laptop personal computer, a tablet computer, a desktop computer or the like. In some embodiments, therapy signals from controller 960 are carried by electrical connection 931 to electrical connector 810 of medical electrode system 801, and then on to electrode 835, which delivers the current load to the patient's tissue.

FIG. 9C is a magnified front view of an electrical stimulation system 903 positioned at eye 98, according to some embodiments of the present invention. In some embodiments, system 903 includes medical electrode system 801 operatively coupled to controller 960. In some embodiments, controller 960 includes a microprocessor (uP) operated by a battery, and optionally is controlled and/or programmed by a nearby laptop personal computer, a tablet computer, a desktop computer or the like. In some embodiments, medical electrode system 801 is electrically coupled to electrical connection 931 that ends at electrical connector 932. In some embodiments, connector 932 plugs into or otherwise electrically connects to a corresponding connector 961 on controller 960.

In some embodiments, the present invention provides a system that includes a first electrode substrate having a first end and a second end, wherein the first electrode substrate includes one or more electrodes on the first electrode substrate, wherein the one or more electrodes are configured to apply electrical-stimulation therapy to a first eye of a patient, the first eye having an upper eyelid and a lower eyelid, wherein the first electrode substrate is configured to locate the one or more electrodes on an outer surface of at least one of the upper eyelid and the lower eyelid of the patient's first eye, a first plurality of adhesive patches coupled to the first electrode substrate and configured to secure the first electrode substrate to the patient, wherein the first plurality of adhesive patches includes a first adhesive patch and a second adhesive patch; and a stimulation controller configured to control the electrical-stimulation therapy, wherein each of the one or more electrodes of the first electrode substrate is operatively coupled to the stimulation controller.

In some embodiments of the system, the first adhesive patch is located at the first end of the first electrode substrate and is configured to couple to a side of a nose of the patient, and wherein the second adhesive patch is located between the first end and the second end of the first electrode substrate and is configured to couple to a temple of the patient. In some embodiments, the first electrode substrate further includes a flexible section configured to adjust a size of the first electrode substrate. In some embodiments, the first plurality of adhesive patches further includes a third adhesive patch configured to secure the one or more electrodes to the outer surface of the at least one of the upper eyelid and the lower eyelid of the patient's first eye. In some embodiments, the first electrode substrate further includes an electrical connector located at the second end of the first electrode substrate, and an electrical pathway on the first electrode substrate, wherein the electrical pathway is configured to electrically couple the one or more electrodes to the electrical connector.

In some embodiments, the system further includes a first return electrode configured to be located on a portion of the patient's neck, wherein the stimulation controller is further configured to control an electrical current between at least one of the one or more electrodes on the first electrode substrate and the first return electrode such that the electrical current passes through a retina of the first eye of the patient. In some embodiments, the system further includes a second electrode substrate having a first end and a second end, wherein the second electrode substrate includes one or more electrodes on the second electrode substrate, wherein the one or more electrodes are configured to apply electrical-stimulation therapy to a second eye of a patient, the second eye having an upper eyelid and a lower eyelid, wherein the second electrode substrate is configured to locate the one or more electrodes on an outer surface of at least one of the upper eyelid and the lower eyelid of the patient's second eye, a second plurality of adhesive patches coupled to the second electrode substrate and configured to secure the second electrode substrate to the patient, wherein the second plurality of adhesive patches includes a third adhesive patch and a fourth adhesive patch; and wherein each of the one or more electrodes of the second electrode substrate is operatively coupled to the stimulation controller.

In some embodiments, the present invention provides a method that includes providing a first electrode substrate having a first end and a second end, wherein the first electrode substrate includes one or more electrodes on the first electrode substrate, wherein the one or more electrodes are configured to apply electrical-stimulation therapy to a first eye of a patient, the first eye having an upper eyelid and a lower eyelid, wherein the first electrode substrate is configured to locate the one or more electrodes on an outer surface of at least one of the upper eyelid and the lower eyelid of the patient's first eye, a first plurality of adhesive patches coupled to the first electrode substrate and configured to secure the first electrode substrate to the patient, wherein the first plurality of adhesive patches includes a first adhesive patch and a second adhesive patch; attaching the first electrode substrate to the patient's skin such that the one or more electrodes are on the outer surface of at least one of the upper eyelid and the lower eyelid of the patient's first eye; and applying the electrical-stimulation therapy to the first eye during a first treatment session.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," " "second," and "third," etc., are used merely as labels, and are not intended to impose numerical requirements on their objects.

What is claimed is:

1. A system comprising:

a first electrode substrate having a first end and a second end, wherein the first electrode substrate includes one or more electrodes on the first electrode substrate, wherein the one or more electrodes are configured to apply electrical-stimulation therapy to a first eye of a patient, the first eye having an upper eyelid and a lower eyelid, wherein the first electrode substrate is configured to locate the one or more electrodes on an outer surface of at least one of the upper eyelid and the lower eyelid of the patient's first eye;

a first plurality of adhesive patches coupled to the first electrode substrate and configured to secure the first electrode substrate to the patient, wherein the first plurality of adhesive patches includes a first adhesive patch and a second adhesive patch, wherein the first adhesive patch is located at the first end of the first electrode substrate and is configured to couple to a side of a nose of the patient, wherein the second adhesive patch is located between the first end and the second end of the first electrode substrate and is configured to couple to a temple of the patient, and wherein the one or more electrodes are located on the first electrode substrate between the first adhesive patch and the second adhesive patch;

a flexible section of the first electrode substrate that is located between the one or more electrodes and the second adhesive patch, wherein the flexible section is stretchable such that a length of the flexible section between the one or more electrodes and the second adhesive patch can be varied to ensure that the system can fit varying patient face sizes; and a stimulation controller configured to control the electrical-stimulation therapy, wherein each of the one or more electrodes of the first electrode substrate is operatively coupled to the stimulation controller.

2. The system of claim 1, wherein the first plurality of adhesive patches further includes a third adhesive patch configured to secure the one or more electrodes to the outer surface of the at least one of the upper eyelid and the lower eyelid of the patient's first eye.

3. The system of claim 1, wherein the first electrode substrate further includes an electrical connector located at the second end of the first electrode substrate, and an electrical pathway on the first electrode substrate extending from the one or more electrodes across the flexible section to the electrical connector.

4. The system of claim 1, further comprising:

a ground electrode configured to provide a return pathway for electrical stimulation signals generated by the one or more electrodes on the first electrode substrate.

5. The system of claim 1, further comprising:

a second electrode substrate having a first end and a second end, wherein the second electrode substrate includes one or more electrodes on the second electrode substrate, wherein the one or more electrodes on the second electrode substrate are configured to apply electrical-stimulation therapy to a second eye of a patient, the second eye having an upper eyelid and a lower eyelid, wherein the second electrode substrate is configured to locate the one or more electrodes on an outer surface of at least one of the upper eyelid and the lower eyelid of the patient's second eye, wherein the second electrode substrate includes a flexible section of the second electrode substrate that is located between the one or more electrodes of the second electrode substrate and the second adhesive patch of the second electrode substrate, wherein the flexible section of the second electrode substrate is stretchable such that a length of the flexible section of the second electrode substrate between the one or more electrodes of the second electrode substrate and the second adhesive patch of the second electrode substrate can be varied; and a second plurality of adhesive patches coupled to the second electrode substrate and configured to secure the second electrode substrate to the patient, wherein the second plurality of adhesive patches includes a first adhesive patch of the second electrode substrate and a second adhesive patch of the second electrode substrate, and wherein each of the one or more electrodes of the second electrode substrate is operatively coupled to the stimulation controller.

6. The system of claim 1, wherein the stimulation controller is operatively coupled to a remote computer device.

7. The system of claim 1, wherein the stimulation controller is a battery-operated unit configured to be located on the patient.

8. The system of claim 1, wherein the first electrode substrate has only a single electrode, and wherein the first plurality of adhesive patches further includes a third adhesive patch configured to secure the single electrode to the outer surface of the at least one of the upper eyelid and the lower eyelid of the patient's first eye.

9. A method comprising:

providing a first electrode substrate having a first end, a second end, and a middle portion located between the first end and the second end, wherein the first electrode substrate includes a first plurality of adhesive patches coupled to the first electrode substrate and configured to secure the first electrode substrate to the patient, wherein the first plurality of adhesive patches includes a first adhesive patch and a second adhesive patch, wherein the first adhesive patch is located at the first end of the first electrode substrate, wherein the second adhesive patch is located between the first end and the second end of the first electrode substrate, wherein the first electrode substrate includes one or more electrodes on the first electrode substrate, wherein the middle portion includes a flexible section of the first electrode substrate that is located between the one or more electrodes and the second adhesive patch, wherein the flexible section is stretchable such that a length of the flexible section between the one or more electrodes and the second adhesive patch can be varied to ensure that the system can fit varying patient face sizes, and wherein the one or more electrodes are configured to apply electrical-stimulation therapy to a first eye of a patient, the first eye having an upper eyelid and a lower eyelid;

placing the first electrode substrate on the patient such that the one or more electrodes are located on an outer surface of at least one of the upper eyelid and the lower eyelid of the patient's first eye;

securing the first electrode substrate to the patient by adhering the first adhesive patch to a side of a nose of the patient and adhering the second adhesive patch to a temple of the patient;

providing a stimulation controller configured to control the electrical-stimulation therapy; and operatively coupling each of the one or more electrodes of the first electrode substrate to the stimulation controller.

10. The method of claim 9, wherein the securing of the first electrode substrate to the patient includes:

adhering the one or more electrodes to the outer surface of the at least one of the upper eyelid and the lower eyelid of the patient's first eye.

11. The method of claim 9, wherein the first electrode substrate further includes an electrical connector located at the second end of the first electrode substrate, the method further comprising:

electrically coupling the one or more electrodes to the electrical connector.

12. The method of claim 9, further comprising:

providing a return pathway for electrical stimulation signals generated by the one or more electrodes on the first electrode substrate.

13. The method of claim 9, further comprising:

providing a second electrode substrate having a first end, a second end, and a middle portion located between the first end and the second end, wherein the second electrode substrate includes one or more electrodes on the second electrode substrate, wherein the second electrode substrate includes a flexible section of the second electrode substrate that is located between the one or more electrodes of the second electrode substrate and the second adhesive patch of the second electrode substrate, wherein the flexible section of the second electrode substrate is stretchable such that a length of the flexible section of the second electrode substrate between the one or more electrodes of the second electrode substrate and the second adhesive patch of the second electrode substrate can be varied, wherein the one or more electrodes of the second electrode substrate are configured to apply electrical-stimulation therapy to a second eye of a patient, the second eye having an upper eyelid and a lower eyelid;

placing the second electrode substrate on the patient such that the one or more electrodes of the second electrode substrate are located on an outer surface of at least one of the upper eyelid and the lower eyelid of the patient's second eye;

securing the second electrode substrate to the patient by adhering the first adhesive patch of the second electrode substrate to a side of a nose of the patient and adhering the second adhesive patch of the second electrode substrate to a temple of the patient; and operatively coupling each of the one or more electrodes of the second electrode substrate to the stimulation controller.

14. The method of claim 9, the method further comprising:

adjusting a size of the first electrode substrate via the flexible section, wherein the securing of the first electrode substrate to the patient includes:

adhering the first end of the first electrode substrate to a side of a nose of the patient;

adhering the middle portion of the first electrode substrate to a temple of the patient; and adhering the one or more electrodes to the outer surface of the at least one of the upper eyelid and the lower eyelid of the patient's first eye.

15. A system comprising:

a first electrode substrate having a first end, a second end, and a middle portion located between the first end and the second end;

means for securing a first end of the first electrode substrate to a patient's nose, and means for securing the middle portion of the first electrode substrate to the patient's temple;

one or more electrodes on the first electrode substrate, wherein the one or more electrodes are configured to apply electrical-stimulation therapy to a first eye of a patient, the first eye having an upper eyelid and a lower eyelid, wherein the middle portion of the first electrode substrate includes a flexible section that is located between the one or more electrodes and the means for securing the first electrode substrate to the patient's temple, and wherein the flexible section is stretchable such that a length of the flexible section can be varied to ensure that the system can fit varying patient face sizes, and wherein the means for securing is configured such that the one or more electrodes are located on an outer surface of at least one of the upper eyelid and the lower eyelid of the patient's first eye;

means for controlling the electrical-stimulation therapy; and means for operatively coupling each of the one or more electrodes of the first electrode substrate to the means for controlling.

16. The system of claim 15, further comprising:

means for securing the one or more electrodes to the outer surface of at least one of the upper eyelid and the lower eyelid.

17. The system of claim 15, wherein the first electrode substrate further includes an electrical connector located at the second end of the first electrode substrate, and an electrical pathway on the first electrode substrate extending from the one or more electrodes across the flexible section to the electrical connector.

18. The system of claim 15, further comprising:

means for returning electrical stimulation signals generated by the one or more electrodes on the first electrode substrate.

19. The system of claim 15, further comprising:

a second electrode substrate having a first end, a second end, and a middle portion located between the first end and the second end;

means for securing a first end of the second electrode substrate to a patient's nose, and means for securing the second electrode substrate to the patient's temple, wherein the second electrode substrate includes one or more electrodes on the second electrode substrate, wherein the second electrode substrate includes a flexible section of the second electrode substrate that is located between the one or more electrodes of the second electrode substrate and the means for securing the second electrode substrate to the patient's temple, wherein the flexible section of the second electrode substrate is stretchable such that a length of the flexible section of the second electrode substrate can be varied, and wherein the one or more electrodes of the second electrode substrate are configured to apply electrical-stimulation therapy to a second eye of a patient, the second eye having an upper eyelid and a lower eyelid; and means for operatively coupling each of the one or more electrodes of the second electrode substrate to the means for controlling.

20. The system of claim 15, wherein the stimulation controller is operatively coupled to a remote computer device.

21. The system of claim 15, wherein the stimulation controller is a battery-operated unit configured to be located on the patient.

22. The system of claim 15, wherein the first electrode substrate has only a single electrode, and wherein the first electrode substrate further includes means for securing the single electrode to the outer surface of the at least one of the upper eyelid and the lower eyelid of the patient's first eye.

* * * * *